United States Patent [19]

Phung

[11] Patent Number: 4,831,153
[45] Date of Patent: May 16, 1989

[54] PREPARATION OF N-VINYL-2-OXAZOLIDINONE

[75] Inventor: K. Van Phung, Midland, Mich.

[73] Assignee: The Dow Chemical Company, Midland, Mich.

[21] Appl. No.: 507,844

[22] Filed: Jun. 27, 1983

[51] Int. Cl.$^4$ .................. C07D 263/04; C07D 263/16
[52] U.S. Cl. ................... 548/231; 548/229; 548/232
[58] Field of Search ............ 548/231, 229, 232

[56] References Cited

U.S. PATENT DOCUMENTS

| | | | |
|---|---|---|---|
| 2,818,362 | 12/1957 | Drechsel | 548/231 |
| 2,891,058 | 6/1969 | Walles et al. | 548/231 |
| 2,905,690 | 9/1957 | Bukke | 548/231 |
| 3,019,231 | 1/1962 | Peppel et al. | 548/231 |
| 3,033,829 | 5/1962 | Bakke | 548/231 |
| 3,064,004 | 11/1982 | Little | 548/239 |

FOREIGN PATENT DOCUMENTS 1273533  3/1969  Fed. Rep. of Germany ...... 548/239

OTHER PUBLICATIONS

Sashio, M. et al., Chem. Absts., 74:125567z, (1971).
Sato, M., Chem. Absts, 59:3908b (1963).
Arend, W. et al., Chem. Absts., 55:5531b.
Sineokov, A. P., Chem. Absts., 76:140614, (1972).
Kutner, A., J. Org. Chem., 26, pp. 3495-3498, (1961).
Dreschel et al., J. Org. Chem, 22, 849-851, (1957).

Primary Examiner—Lorraine T. Kendell

[57] ABSTRACT

This invention is a process for the preparation of N-vinyl-2-oxazolidinones which comprises pyrolyzing a N-(1-hydroxyalkyl)-2-oxazolidinone or the N-(1-hydrocarbyloxyalkyl)-2-oxazolidinone under conditions such that the hydroxy or hydrocarbyloxy moiety is removed to prepared a N-vinyl-2-oxazolidinone.

28 Claims, No Drawings

PREPARATION OF N-VINYL-2-OXAZOLIDINONE

BACKGROUND OF THE INVENTION

This invention relates to a process for the preparation of N-vinyl-2-oxazolidinone.

N-vinyl-2-oxazolidinones are useful in the preparation of polymers and such polymers are useful as complexing agents for a wide range of phenolic compounds and dyes, and in the preparation of plastics. In addition, they are useful in coating compositions and in adhesives and are valuable intermediates for dye-stuffs, dye receptors and textile assistants.

There are several known methods for the preparation of N-vinyl-2-oxazolidinone.

Arend et al., German Pat. No. 972,304, teach a three-step synthesis in which the last step comprises the dehydrochlorination of N-(2-chloroethyl)-2-oxazolidinone in the presence of $Na_2O$. Dreschel, *J. Org. Chem.*, 22, 849 (1957), teaches a three-step preparation of N-vinyl-2-oxazolidinone in which the last step comprises dehydrochlorination of N-(2-chloroethyl)-2-oxazolidinone in the presence of potassium t-butoxide. These dehydrochlorination processes are disadvantageous because they involve a multistep synthesis of N-vinyl-2-oxazolidinone and the yields are poor.

Kutner, *J. Org. Chem.*, 26, 3465 (1961), discloses a three-step synthesis of N-vinyl-2-oxazolidinone in which the last step comprises the pyrolysis of N-(2-acetoxyethyl)-2-oxazolidinone at a temperature of 580° C. These conditions are very severe, and the oxazolidinone ring is susceptible to decomposition under such conditions.

Bakke, U.S. Pat. No. 3,033,829, discloses a process in which 2-oxazolidinone is transvinylated with a vinyl ether in the presence of a mercury catalyst to prepare a N-vinyl-2-oxazolidinone. This process involves the preparation of large amounts of acetal as a by-product along with the reduction of some of the mercury catalyst to elemental mercury which creates environmental problems.

Bakke, U.S. Pat. No. 2,905,690, discloses the preparation of N-vinyl-2-oxazolidinone by the Reppe synthesis. In particular, a 2-oxazolidinone is converted to its sodium salt by treatment with metallic sodium which is then vinylated with acetylene. This process is disadvantageous because it requires the use of high pressure and acetylene which creates a risk of explosion.

Ingleby, U.S. Pat. No. 3,346,586, discloses that the condensation product of 1 mole of an aldehyde and two moles of a 2-oxazolidinone can be decomposed to prepare one mole of N-vinyl-2-oxazolidinone and one mole of 2-oxazolidinone. The process involves heating the condensation product at reduced pressure, optionally in the presence of an acid catalyst. This process suffers from the disadvantage that low yields of the desired N-vinyl-2-oxazolidinone are achieved. In particular, it takes at least two moles of 2-oxazolidinone to prepare one mole of N-vinyl-2-oxazolidinone.

Seneokor et al., *Khim. Geterotsikl Soedin*, 275–7 (1970), teach that N-vinyl-2-oxazolidinone can be prepared by reacting vinylisocyanate with alkylene oxides. The instability and low availability of vinylisocyanate renders this process disadvantageous.

Prior to the invention disclosed herein, the skilled artisan was confronted with several problems in the preparation of N-vinyl-2-oxazolidinone. The formation of a N,N'-alkylidene-bis(2-oxazolidinone) under certain conditions is one such problem. Under acidic conditions, the N-vinyl-2-oxazolidinone undergoes decomposition to the starting 2-oxazolidinone. Further, 2-hydroxyethyl-2-oxazolidinone, an intermediate in the preparation of N-vinyl-2-oxazolidinone, is not thermally stable and undergoes decomposition. The prior art processes described herein often result in low yields of the desired product.

What is needed is a process for the preparation of N-vinyl-2-oxazolidinones in which the formation of the N,N'-alkylidene-bis(2-oxazolidinones) is prevented or minimized, and the decomposition of the product is prevented. What is further needed is a process in which no by-products are prepared which create environmental problems or create a danger of explosion. What is also needed is a reasonably simple process in which high yields of product can be achieved.

SUMMARY OF THE INVENTION

This invention is a process for the preparation of N-vinyl-2-oxazolidinones which comprises pyrolyzing a N-(1-hydroxyalkyl)-2-oxazolidinone or a N-(1-hydrocarbyloxyalkyl)-2-oxazolidinone under conditions such that the hydroxy or hydrocarbyloxy moiety is removed to prepare a N-vinyl-2-oxazolidinone.

Surprisingly, this process results in a much lower formation of the N,N'-alkylidene-bis(2-oxazolidinone by-products. Further, decomposition of the N-vinyl-2-oxazolidinone under reaction conditions is prevented.

This process does not involve the use of explosive conditions or result in the preparation of environmentally undesirable by-products.

DETAILED DESCRIPTION OF THE INVENTION

The N-vinyl-2-oxazolidinones prepared by this process include those corresponding to the formula

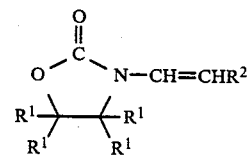

wherein $R^1$ is hydrogen, $C_{1-20}$ hydrocarbyl or $C_{1-20}$ hydrocarbyl substituted with a halo, carbonyl, alkoxy, carbonylalkoxy, nitro or cyano group; and $R^2$ is hydrogen or a $C_{1-20}$ hydrocarbyl group.

In the above formula $R^1$ is preferably hydrogen, $C_{1-10}$ alkyl, $C_{1-10}$ haloalkyl, phenyl or benzyl and more preferably hydrogen, methyl, ethyl, propyl or butyl. $R^2$ is preferably hydrogen or $C_{1-10}$ alkyl, and more preferably hydrogen.

In one preferred embodiment, each $R^1$ on the 4 carbon is hydrogen and each $R^1$ on the 5 carbon is separately in each occurrence hydrogen or $C_{1-10}$ alkyl. In this embodiment, it is more preferred if one $R^1$ on the 5 carbon is hydrogen while the other $R^1$ is $C_{1-10}$ alkyl.

Among preferable N-vinyl-2-oxazolidinones are N-vinyl-2-oxazolidinone, N-vinyl-5,5-dimethyl-2-oxazolidinone, N-vinyl-5-methyl-5-ethyl-2-oxazolidinone, N-vinyl-5-methyl-5-propyl-2-oxazolidinone, N-vinyl-5-methyl-5-butyl-2-oxazolidinone, N-vinyl-5-methyl-5-pentyl-2-oxazolidinone, N-vinyl-5-methyl-5- hexyl-2-oxazolidinone, N-vinyl-5-methyl-5-heptyl-2-oxazolidinone, N-vinyl-5-octyl-2-oxazolidinone, N-vinyl-5-methyl-5-nonyl-2-oxazolidinone, N-vinyl-5-methyl-5-decyl-2-oxazolidinone, N-vinyl-5,5-diethyl-2-oxazolidinone, N-vinyl-5-ethyl-5-methyl-2-oxazolidinone, N-vinyl-5-ethyl-5-propyl-2-oxzolidinone, N-vinyl-5-ethyl-5-butyl-2-oxazolidinone, N-vinyl-5-ethyl-5-pentyl-2-oxazolidinone, N-vinyl-5-ethyl-5-hexyl-2-oxazolidinone, N-vinyl-5-ethyl-5-heptyl-2-oxazolidinone, N-vinyl-5-ethyl-5-octyl-2-oxazolidinone, N-vinyl-5-ethyl-5-nonyl-2-oxazolidinone, N-vinyl-5-ethyl-5-decyl-2-oxazolidinone, N-vinyl-5,5-dipropyl-2-oxazolidinone, N-vinyl-5-propyl-5-butyl-2-oxazolidinone, N-vinyl-5-methyl-2-oxazolidinone, N-vinyl-5-ethyl-2-oxazolidinone, N-vinyl-5-propyl-2-oxazolidinone, N-vinyl-5-butyl-2-oxazolidinone, N-vinyl-5-pentyl-2-oxazolidinone, N-vinyl-5-hexyl-2-oxazolidinone, N-vinyl-5-heptyl-2-oxazolidinone, N-vinyl-5-octyl-2-oxazolidinone, N-vinyl-5-nonyl-2-oxazolidinone, and N-vinyl-5-decyl-2-oxazolidinone. More preferred N-vinyl-2-oxazolidinones include N-vinyl-2-oxazolidinone, N-vinyl-5,5-dimethyl-2-oxazolidinone, N-vinyl-5-methyl-5-ethyl-2-oxazolidinone, N-vinyl-5,5-diethyl-2-oxazolidinone, N-vinyl-5-methyl-2-oxazolidinone, N-vinyl-5-ethyl-2-oxazolidinone, N-vinyl-5-propyl-2-oxazolidinone, N-vinyl-5-butyl-2-oxazolidinone, N-vinyl-5-pentyl-2-oxazolidinone, N-vinyl-5-hexyl-2-oxazolidinone, N-vinyl-5-heptyl-2-oxazolidinone, N-vinyl-5-octyl-2-oxazolidinone, N-vinyl-5-nonyl-2-oxazolidinone, N-vinyl-5-decyl-2-oxazolidinone.

Even more preferred are N-vinyl-2-oxazolidinone, N-vinyl-5-methyl-2-oxazolidinone, N-vinyl-5-ethyl-2-oxazolidinone, N-vinyl-5-propyl-2-oxazolidinone and N-vinyl-5-butyl-2-oxazolidinone.

Hydrocarbyl means herein an organic radical containing carbon and hydrogen atoms. The term hydrocarbyl includes the following organic radicals: alkyl, alkenyl, alkynyl, cycloalkyl, cycloalkenyl, aryl, aliphatic and cycloaliphatic, aralkyl and alkaryl. Aliphalic refers herein to straight-, branched- and saturated and unsaturated hydrocarbon chains, that is, alkyl, alkenyl or alkynyl. Cycloaliphatic refers herein to saturated and unsaturated cyclic hydrocarbons, that is, cycloalkenyl and cycloalkyl. The term aryl refers herein to biaryl, biphenylyl, phenyl, naphthyl, phenanthranyl, anthranyl and two aryl groups bridged by an alkylene group. Alkaryl refers herein to an alkyl-, alkenyl- or alkynyl-substituted aryl substituent wherein aryl is as defined hereinbefore. Aralkyl means herein an alkyl, alkenyl or alkynyl group substituted with an aryl group, wherein aryl is as defined hereinbefore. Alkyl includes straight- and branched-chain methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl groups. Alkenyl includes straight- and branched-chain ethenyl, propenyl, butenyl, pentenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl groups and the like. Alkenyl further refers to the above-namded groups in which there are two or more double bonds, for example, butadiene, pentadiene, hexadiene, heptadiene and the like. Alkynyl groups include straight- and branched-chain ethynyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl groups and the like. Alkynyl further refers to the above-named groups wherein there are two or more triple bonds.

Cycloalkyl refers to alkyl groups containing one, two, three or more cyclic rings including cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentadecyl, cyclohexadecyl, cycloheptadecyl, cyclooctadecyl, cyclononadecyl, cycloeicosyl, bicyclopropyl, bicyclobutyl, bicyclopentyl, bicyclohexyl, bicycloheptyl, bicyclooctyl, bicyclononyl, bicyclodecyl, tricyclopropyl, tricyclobutyl, tricyclopentyl, tricyclohexyl groups and groups containing two or more of the cycloalkyl groups named hereinbefore. Cycloalkenyl refers to mono-, di- and polycyclic groups containing one or more double bonds including cyclopropenyl, cyclobutenyl, cyclopentenyl, cyclohexenyl, cycloheptenyl, cyclooctenyl, cyclononenyl, cyclodecenyl, cycloundecenyl, cyclododecenyl, cyclotridecenyl, cyclotetradecenyl, cyclopentadecenyl, cyclohexadecenyl, cycloheptadecenyl, cyclooctadecenyl, cyclononadecenyl, cycloeicosenyl, bicyclopropenyl, bicyclobutenyl, bicyclopentenyl, bicycloheptenyl, bicyclooctenyl, bicyclononenyl, bicyclopentenyl, tricyclopropenyl, tricyclobutenyl, tricyclopentenyl and tricyclohexenyl groups. Cycloalkenyl also refers to the above-named cycloalkenyl groups wherein two or more double bonds are present, for example, cyclobutadienyl, cyclopentadienyl and cyclohexadienyl groups.

The N-(1-hydroxyalkyl)-2-oxazolidinones and N-(1-hydrocarbyloxyalkyl)-2-oxazolidinones which are pyrolyzed in this invention include those which correspond to the formula

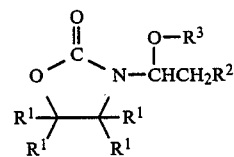

II wherein $R^1$ and $R^2$ are as defined hereinbefore, and $R^3$ is separately in each occurrence hydrogen or a $C_{1-20}$ hydrocarbyl group. $R^3$ is preferably hydrogen, $C_{1-10}$ alkyl or $C_{3-10}$ cycloalkyl, and more preferably methyl, ethyl, propyl, butyl, cyclopentane or cyclohexane.

Among the preferred N-(1-hydroxyalkyl)-2-oxazolidinones are N-(1-hydroxyethyl)-2-oxazolidinone, N-(1-hydroxyethyl)-5-methyl-2-oxazolidinone, N-(1-hydroxyethyl)-5-ethyl-2-oxazolidinone and N-(1-hydroxyethyl)-5-propyl-2-oxazolidinone, while N-(1-hydroxyethyl)-5-ethyl-2-oxazolidinone and N-(1-hydroxyethyl)-5-propyl-2-oxazolidinone are more preferred. Among the preferred N-(1-hydrocarbyloxyalkyl)-2-oxazolidinones are N-(1-methoxyethyl)-2-oxazolidinone, N-(1-ethoxyethyl)-2-oxazolidinone, N-(1-propoxyethyl)-2-oxazolidinone, N-(1-butoxyethyl)-2-oxazolidinone, N-(1-methoxyethyl)-5-methyl-2-oxazolidinone, N-(1-ethoxyethyl)-5-methyl-2-oxazolidinone, N-(1-propoxyethyl)-5-methyl-2-oxazolidinone, N-(1-isopropoxyethyl)-5-methyl-2-oxazolidinone, N-(1-butoxyethyl)-5-methyl-2-oxazolidinone, N-(1-methoxyethyl)-5-ethyl-2-oxazolidinone, N-(1-ethoxyethyl)-5-ethyl-2-oxazolidinone, N-(1-propoxyethyl)-5-ethyl-2-oxazolidinone, N-(1-isopropoxyethyl)-5-ethyl-2- oxazolidinone and N-(1-butoxyethyl)-5-ethyl-2-oxazolidinone.

The N-(1-hydroxyalkyl)-2-oxazolidinones are prepared by contacting an aldehyde with a 2-oxazolidinone. This process can be represented by the following equation Equation 1

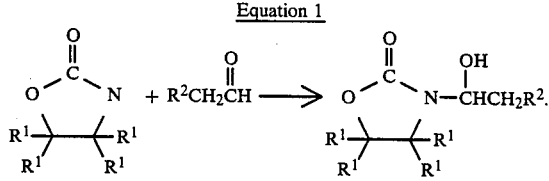

Thus, an oxazolidinone is contacted with an aldehyde at a temperature of between about 0° C. to 100° C. at a pH of between 1 and 7. Preferable temperatures are between about 20° C. and 40° C. with 20° C. to 25° C. most preferred. A pH of between 6 and 7 is preferred. The pH can be adjusted by addition of an inorganic acid such as hydrochloric acid, sulfuric acid, nitric acid or phosphoric acid.

In the embodiment wherein the 2-oxazolidinone is 2-oxazolidinone or 5-methyl-2-oxazolidinone, the N,N'alkylidene-bis(2-oxazolidinone) adduct is a major by-product, thus a pH of 6 to 7 is preferred for this embodiment. The formation of the alkylidene-bis(2-oxazolidinone) is negligible wherein one $R^1$ on the carbon atom on the 5-carbon is an alkyl group containing two or more carbon atoms.

Generally between about 3 and 5 moles of aldehyde per mole of 2-oxazolidinone is used, as it usually takes at least 3 moles of aldehyde to get complete conversion of 2-oxazolidinone. Between about 4 and 5 moles of aldehyde per mole of 2-oxazolidinone are preferred. The excess aldehyde functions as the solvent in this process. The excess aldehyde is stripped off to recover the product.

The N-(1-hydrocarbyloxyalkyl)-2-oxazolidinones are prepared by contacting a solution of 2-oxazolidinone in an alcohol with an acetal or hemiacetal. This process is illustrated by the following equation Equation 2

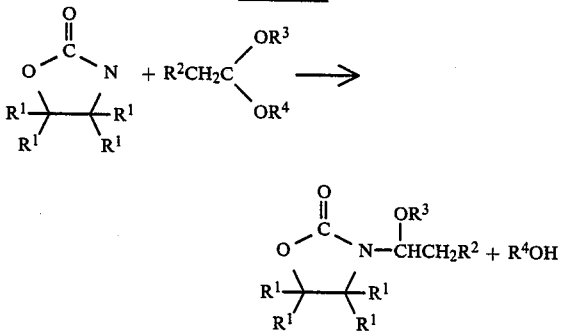

wherein $R^1$, $R^2$ and $R^3$ are as described hereinbefore and $R^4$ is $R^3$ or H.

Between about 2 and 5 moles of hemiacetal or acetal per mole of oxazolidinone is generally used preferably between about 2 to 3 moles of hemiacetal or acetal per mole of 2-oxazolidinone is used.

The reaction temperature is any temperature at which the reaction means is suitable, usually between about 0° C. and 100° C., preferably between about 20° C. and 40° C. and most preferably 20° C. to 25° C. The reaction takes place under acidic conditions, at a pH of between 1 and 7, preferably between 6 and 7. Reaction times are between 12 and 48 hours, preferably between 16 and 24 hours. After the reaction goes to completion, the solution is neutralized with an alkali metal alkoxide. The unreacted acetal or hemiacetal and alcohol are stripped off to recover the product.

The hemiacetals can be prepared by adding an aldehyde to an alcohol which has been acidified to a pH of about 1 with a solution of acid in methanol. Suitable acids are inorganic acids such as hydrochloric acid, sulfuric acid, nitric acid and phosphoric acid. Usually a mole ratio of alcohol to aldehyde of 1.5:1 to 2.0:1. The reaction is exothermic and thus is cooled to keep the temperature below 35° C. The acetals are prepared under the same conditions except a mole ratio of alcohol to aldehyde of 3.0:1 to 4.0:1 is used.

The N-vinyl-2-oxazolidinones are prepared by pyrolysis of the N-(1-hydroxyalkyl)-2-oxazolidinones or N-(1-hydroxycarbyloxy)-2-oxazolidinones. Any temperature at which the elimination of water or an alcohol occurs to form a vinyl group is suitable for this reaction. Desirable temperatures are between about 200° C. and 500° C. The reaction is preferentially done in an inert atmosphere, that is, in the absence of oxygen under an inert gas. Desirable inert gases include nitrogen, argon and the like.

A preferred mode of pyrolysis involves the use of a hot tube reactor packed with suitable packing. Suitable packings are those which are stable at pyrolysis conditions and inert to the reactants. Among suitable packings are glass beads, stainless steel helices and Carborundum ® beads. The purpose of the packing is to prevent the reactants from passing through the hot tube too fast.

It is desirable to pass an inert gas through the hot tube during the reaction so as to push the vaporized reactants and products through the hot tube.

In some cases complete pyrolysis does not occur in one pass of the reactants through the hot tube. Thus, it may be advantageous to pass the reactants through the hot tube two or more times until an acceptable conversion is reached.

A suitable pressure is that pressure at which the reaction occurs. Preferable pressures are between about 10 and 760 mm Hg. Generally, any pyrolysis time at which the reaction occurs is suitable, preferably between about 1 and 120 seconds, more preferably between 1 and 10 seconds.

When a N-(1-hydroxyalkyl)-2-oxazolidinone is pyrolyzed by this process, water is eliminated to prepare the N-vinyl-2-oxazolidinone. Whereas when a N-(1-hydrocarbyloxyalkyl)-2-oxazolidinone is pyrolyzed, alcohol is eliminated to prepare the N-vinyl-2-oxazolidinone.

It is preferred to prepare the N-vinyl-2-oxazolidinone by pyrolysis of the N-(1-hydrocarbyloxyalkyl)-2-oxazolidinone. This is because the reaction in which 2-oxazolidinone and acetaldehyde are used to prepare the N-(1-hydroxyalkyl)-2-oxazolidinone is an equilibrium reaction, and under certain pyrolysis conditions this compound will undergo aldehyde elimination instead of water elimination to prepare the 2-oxazolidinone instead of the N-vinyl-2-oxazolidinone. This can significantly reduce the yields.

In the pyrolysis of the N-(1-hydrocarbyloxyalkyl)-2-oxazolidinone, a pH of between about 2 and 7 is preferred. Below a pH of 6, the alkylidene-bis(2-oxazolidinone) by-product is produced in significant amounts. At a pH of above 7, the N-(1-hydrocarbyloxyalkyl)-2-oxazolidinone is resistant to alcohol elimination. Preferable temperatures for alcohol elimination are between about 200° C. and 500° C., more preferably between about 250° C. and 350° C. Preferred pressures are between about 40 and 300 mm Hg. It has been found that larger hydrocarbyl radicals result in faster and easier eliminations of the alcohol.

The pyrolysis of the N-(1-hydrocarbyloxyalkyl)-2-oxazolidinone can be done in the presence of a dealcoholation catalyst. When a catalyst is used it is preferable that the catalyst be placed on a support. In the case of pyrolysis in a hot tube, the catalyst is supported by coating the packing with the catalyst. Desirable dealcoholation catalysts include weak acids or metal salts of weak acids, for example, potassium bisulfate, sodium bisulfate, copper sulfate or boric acid.

The pyrolysis of the N-(1-hydroxyalkyl)-2-oxazolidinone can be done at any temperature at which dehydration to prepare the vinyl derivative occurs. The temperature is preferably between about 200° C. and 500° C., and more preferably between about 200° C. and 300° C. The pressure is preferably between about 10 and 500 mm Hg.

For the pyrolysis of the N-(1-hydroxyalkyl)-2-oxazolidinone, a pH of between 6 and 7 is preferred. Below a pH of 6, the alkylidene-bis(2-oxazolidinone) by-product is produced in significant amounts. At a pH of above 7, the N-(1-hydroxyalkyl)-2-oxazolidinone is resistant to hydroxyl elimination.

The pyrolysis of the N-(1-hydroxyalkyl)-2-oxazolidinone can be performed in the presence of a dehydration catalyst. It is preferable that the catalyst be on a support. In the embodiment wherein a hot tube reactor is used, the catalyst is preferably supported by the packing. This can be done by coating the packing with the catalyst. Desirable dehydration catalysts are weak acids or metal salts of weak acids, for example, potassium bisulfate, sodium bisulfate, copper sulfate or boric acid.

This process significantly reduces or eliminates the formation of the alkylidene-bis(2-oxazolidinone) by-products. Specifically this process results in the formation of less than 10 percent of the alkylidene-bis(2-oxazolidinone) by weight of the starting material, preferably less than 5 percent. This process results in higher yields of the N-vinyl-2-oxazolidinone than are generally prepared by the prior art processes. Decomposition of the N-vinyl-2-oxazolidinone under reaction conditions are avoided by this process. This process further substantially prevents the decomposition of the starting materials to 2-oxazolidinone.

Specific Embodiments

The following examples are included for illustrative purposes only, and do not limit the scope of the claims of the invention. All parts and percentages are by weight unless otherwise specified. In the examples conversion is calculated by dividing the amount of reactants which are converted to products and by-products by the amount of reactants used, and yield is calculated as the amount of desired product divided by the total amount of products and by-products.

The Pyrolysis Procedure

The dehydration and the dealcoholation are conducted in a continuous manner in a 1"×12" quartz tube. The tube is heated by an electric furnace. The temperature is controlled by a thermocouple well built inside the tube. A dropping funnel and a nitrogen inlet are put on the top of the tube, receivers with outlet are connected to a pressure gauge and vacuum pump. The receivers are cooled by a dry ice/$CH_2Cl_2$ mixture. The tubes are filled with Carborundum ® beads or stainless steel helices. They can be coated with well-known catalysts for the dehydration or dealcoholation. Due to the fluid nature of 3-(1-hydroxyethyl) and 3-(1-alkoxyethyl)-5-alkyl-2-oxazolidinone, the dehydration as dealcoholation proceeds simply by dropping the liquid through the heated tube.

EXAMPLE 1

In a 250-ml capped bottle 35 g (0.3 mole) of 5-ethyl-2-oxazolidinone is dissolved in 60 g (1.36 moles) of cooled acetaldehyde. Concentrated HCl (0.2 ml) is added and the solution is stirred magnetically at room temperature (25° C.) for 48 hours. The unreacted acetaldehyde is removed under vacuum to yield a red colored liquid which weighs 48 g, which represents a 90 percent conversion to the 3-(1-hydroxyethyl)-5-ethyl-2-oxazolidinone.

This derivative is added dropwise to a 12"×1" quartz tube filled with an inert packing stainless steel helices. The tube is preheated to 260° C. and a continuous $N_2$ flow prevents the build-up of vapor in the head space. A dark red mixture is collected from the dry ice cooled receiver. The fractionation by distillation of the mixture over $NaHCO_3$ gives 22 g of N-vinyl-5-ethyl-2-oxazolidinone and 7 g of unreacted 5-ethyl-2-oxazolidinone. The yield is 65 percent based on 81 percent conversion of the 5-ethyl-2-oxazolidinone.

EXAMPLE 2

3-(1-Hydroxyethyl)-5-ethyl-2-oxazolidinone is prepared from 72 g (0.626 mole) of 5-ethyl-2-oxazolidinone by the procedure described in Example 1. A total of 96 g of 3-(1-hyroxyethyl)-5-ethyl-2-oxazolidinone is obtained (87 percent conversion). The 3-(1-hydroxyethyl)-5-ethyl-2-oxazolidinone is dehydrated in the hot tube filled with steel helices which is coated with a catalyst of $NaHSO_4$. The dehydration is conducted at 260° C. under 40 mm Hg pressure. A dark red liquid (83 g) is collected which gives 64.6 g of N-vinyl-5-ethyl-2-oxazolidinone and 10.4 g of 5-ethyl-2-oxazolidinone upon fractionation. The yield is 87 percent based on 86 percent conversion of 5-ethyl-2-oxazolidinone.

EXAMPLE 3

In a three-necked flask equipped with a mechanical stirrer and reflux condenser, ethanol is acidified to a pH of 0.5–1.5 with 8 percent methanolic HCl. To the cooled alcohol is added acetaldehyde. The addition is so conducted that the temperature of the mixture stays under 40° C. The solution is stirred at room temperature for 2 hours after the completion of addition. The mole ratio of alcohol to acetaldehyde is about 1.5:1. 5-Ethyl-2-oxazolidinone (mole ratio of acetaldehyde to 2-oxazolidinone is 3:1) is added dropwise to the solution. The mixture is then stirred for 24 hours at 45° C. The mixture is then neutralized to a pH of 6.5–8 with a solution of sodium methoxide. After removing the unconsumed hemiacetal and alcohol under vacuum, the liquid 3-(1-ethoxyethyl)-5-ethyl-2-oxazolidinone is obtained.

EXAMPLE 4

A 46 g sample of 3-(1-ethoxyethyl)-5-ethyl-2-oxazolidinone (prepared by the method described in Example 3) is passed through the hot tube (filled with steel helices) which is preheated at 260° C. and under a pressure of 150-200 mm and a constant $N_2$ flow. After two passes, 30 g of a yellow liquid is obtained which is fractionated to give 26 g (0.184 mole) of N-vinyl-5-ethyl-2-oxazolidinone and 3 g of 5-ethyl-2-oxazolidinone. The yield of N-vinyl-5-ethyl-2-oxazolidinone is 75 percent.

EXAMPLE 5

A 30 g (0.17 mole) sample of 3-(1-ethoxyethyl)-5-methyl-2-oxazolidinone is dealcoholated as in Example 4 at 260° C./100 mm. After 4 passes through the hot tube, 20 g of a dark yellow liquid is collected from which 17.8 g (0.14 mole) of N-vinyl-5-methyl-2-oxazolidinone is obtained by distillation. The residue contains in large part the unconsumed 3-(1-ethoxyethyl) compound and some impurities. The yield of N-vinyl-5-methyl-2-oxazolidinone is 82 percent.

EXAMPLE 6

Several 3-(1-hydrocarbyloxyethyl)-5-alkyl-2-oxazolidinones were pyrolyzed by the procedure described in Examples 4 and 5. The results are compiled in Table I.

TABLE I

| 5-Alkyl Substituent | Hydrocarbyl Radical | Temp (°C.) | P (Torr) | % Conversion (after 4th pass) | % Yield |
|---|---|---|---|---|---|
| ethyl | methyl | 280 | 60 | 69 | 95 |
| ethyl | ethyl | 280 | 60 | 80 | 95+[1] |
| ethyl | n-propyl | 280 | 60 | 82 | 95 |
| ethyl | n-propyl | 280 | 100 | 94[2] | 95+[1] |
| ethyl | n-propyl | 280 | 60 | 20 | 96 |
| ethyl | butyl | 280 | 60 | 95 | 92 |
| methyl | methyl | 280 | 60 | 46 | 96 |
| methyl | ethyl | 280 | 60 | 75 | 95+[1] |
| methyl | propyl | 280 | 60 | 40 | 95 |
| methyl | butyl | 280 | 60 | 24 | 97 |
| hydrogen | cyclopentyl | 280 | 60 | 18 | 94 |
| hydrogen | methyl | 280 | 60 | 12 | 80[3] |

[1] not taken into account the quantity of bisadduct formed during the pyrolysis
[2] at 3rd pass
[3] no bisadduct was detected, but an increase in the formation of 2-oxazolidinone was observed The data demonstrates that the process works to prepare N-vinyl-2-oxazolidinones with different substituents on the 5 carbon. It further demonstrates the various hydrocarbyl groups which can be removed. It also shows that the 5-ethyl species gives good yields.

EXAMPLE 7

3-(1-Hydroxyethyl)-5-ethyl-2-oxazolidinone was dehydrated by the pyrolysis procedure described in Example 2, wherein the hot tube is packed with steel helices with and without a catalyst. Table II describes the conditions and results

TABLE II

Dehydration of 3-(1-hydroxyethyl)-5-ethyl-2-oxazolidinone

| Run | Catalyst[1] | Temp (°C.) | Pressure (torr) | % Conversion | % Yield[2] |
|---|---|---|---|---|---|
| 1 | no | 260 | 40 | 79 | 61 |
| 2 | yes | 260 | 100 | 84 | 65 |
| 3 | yes | 260 | 40 | 85 | 86 |

[1] The catalyst is $NaHSO_4$ which is supported on the steel helices.
[2] Based on 5-ethyl-2-oxazolidinone.

This data demonstrates that a catalyst is not necessary, but that the catalyst increases the conversion.

What is claimed is:

1. A process for the preparation of n-vinyl-2-oxazolidinone which comprises pyrolyzing at a temperature in the range from 200° C. to about 500° C. and at a pH of between about 6 and 7 a N-(1-hydroxyalkyl)-2-oxazolidinone or a N-(1-hydrocarbyloxyalkyl)-2-oxazolidinone under conditions such that the hydroxy or hydrocarbyloxy moiety is removed to prepare a N-vinyl-2-oxazolidinone wherein less than about 5 percent based on the weight of the starting material of an alkylidene-bis(2-oxazolidinone) is formed.

2. The process of claim 1 wherein the pyrolysis is done in a hot tube reactor packed with a suitable inert packing.

3. The process of claim 2 wherein an inert gas is passed through the hot tube during pyrolysis.

4. The process of claim 3 wherein the residence time is between about 1 and 120 seconds.

5. The process of claim 4 wherein the reaction pressure is between about 10 and 760 mm Hg.

6. The process of claim 5 wherein a N-(1-hydrocarbyloxyalkyl)-2-oxazlidinone is pyrolyzed.

7. The process of claim 6 wherein the pyrolysis temperature is between about 250° C. and 350° C.

8. The process of claim 6 wherein the inert packing is coated with a dealcoholation catalyst.

9. The process of claim 8 wherein the catalyst is a weak acid.

10. The process of claim 9 wherein the catalyst is potassium bisulfate, sodium bisulfate, copper sulfate or boric acid.

11. The process of claim 6 wherein the reaction pressure is between about 40 and 300 mm Hg.

12. The process of claim 1 wherein a N-(1-hydroxyalkyl)-2-oxoazolidinone is pyrolyzed.

13. The process of claim 12 wherein the pyrolysis temperature is between about 200° C. and 300° C.

14. The process of claim 12 wherein the inert packing further comprises a dehydration catalyst.

15. The process of claim 14 wherein the catalyst is a weak acid.

16. The process of claim 15 wherein the catalyst is potassium bisulfate, sodium bisulfate, copper sulfate or boric acid.

17. The process of claim 12 wherein the pyrolysis pressure is between about 10 and 500 mm Hg.

18. The process of claim 1 wherein the 2-oxazolidinones correspond to the formula

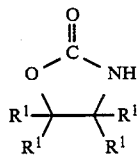

the N-(1-hydroxyalkyl)-2-oxazolidinones and N-(1-hydroxycarbyloxyalkyl)-2-oxazolidinones correspond to the formula

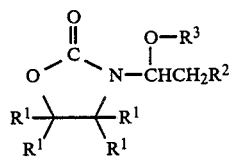

and the N-vinyl-2-oxazolidinone corresponds to the formula

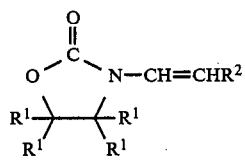

wherein $R^1$ is separately in each occurrence hydrogen, $C_{1-20}$ hydrocarbyl or $C_{1-20}$ hydrocarbyl substituted with a halo, carbonyl, alkoxy, carbonylalkoxy, nitro or cyano group;

$R^2$ is separately in each occurrence hydrogen or a $C_{1-20}$ hydrocarbyl group; and $R^3$ is separately in each occurrence hydrogen or a $C_{1-20}$ hydrocarbyl group.

19. The process of claim 18 wherein $R^1$ is hydrogen, $C_{1-10}$ alkyl, $C_{1-10}$ haloalkyl, phenyl or benzyl.

20. The process of claim 19 wherein $R^1$ is hydrogen, methyl, ethyl, propyl or butyl.

21. The process of claim 18 wherein $R^2$ is hydrogen or $C_{1-10}$ alkyl.

22. The process of claim 21 wherein $R^2$ is hydrogen.

23. The process of claim 18 wherein $R^3$ is hydrogen, $C_{1-10}$ alkyl or $C_{3-10}$ cycloalkyl.

24. The process of claim 23 wherein $R^3$ is methyl, ethyl, propyl, butyl, cyclopentane or cyclohexane.

25. The process of claim 1 wherein the N-(1-hydrocarbyloxyalkyl)-2-oxazolidinone and the N-(1-hydroxyalkyl)-2-oxazolidinone are prepared by contacting an aldehyde, acetal or hemiacetal with a 2-oxazolidinone in a suitable solvent at a pH of between about 6 and 7 at a temperature of between about 0° C. and 100° C. under conditions such that a N-(2-hydrocarbyloxyalkyl)-2-oxazolidinone or a N-(1-hydroxyalkyl)-2-oxazolidinone is prepared.

26. The process of claim 25 wherein the molar ratio of aldehyde, acetal or hemiacetal to 2-oxazolidinone is between about 3:1 and 5:1.

27. The process of claim 25 wherein the temperature is between about 20° C. and 40° C.

28. The process of claim 25 wherein an acetal or hemiacetal is contact with a 2-oxazolidinone to prepare a N-(1-hydrocarbyloxyalkyl)-2-oxazolidinone.

* * * * *